United States Patent
Wang et al.

(10) Patent No.: US 11,851,408 B2
(45) Date of Patent: Dec. 26, 2023

(54) METHOD FOR PREPARING PYRIDINE COMPOUND SUBSTITUTED WITH TRIFLUOROMETHYLTHIO, DIFLUOROMETHYLTHIO OR TRIFLUOROMETHYL IN META POSITION

(71) Applicant: NANKAI UNIVERSITY, Tianjin (CN)

(72) Inventors: Xiaochen Wang, Tianjin (CN); Xinyue Zhou, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 18/221,902

(22) Filed: Jul. 14, 2023

(65) Prior Publication Data

US 2023/0365502 A1   Nov. 16, 2023

Related U.S. Application Data

(63) Continuation of application No. PCT/CN2022/099346, filed on Jun. 17, 2022.

(30) Foreign Application Priority Data

May 12, 2022  (CN) .......................... 202210519999.5

(51) Int. Cl.
*C07D 213/70* (2006.01)
*B01J 31/14* (2006.01)

(52) U.S. Cl.
CPC .......... *C07D 213/70* (2013.01); *B01J 31/146* (2013.01)

(58) Field of Classification Search
CPC .............................. C07D 213/70; B01J 31/146
See application file for complete search history.

(56) References Cited

PUBLICATIONS

Yang et al., 141 J. Am. Chem. Soc. 7972-7979 (2019) (Year: 2019).*
Merle Arrowsmith, et al., Magnesium-Catalyzed Hydroboration of Pyridines, Organometallics, 2011, pp. 5556-5559, vol. 30.
Fionn O'Hara, et al., Radical-Based Regioselective C-H Functionalization of Electron-Deficient Heteroarenes: Scope, Tunability, and Predictability, J. Am. Chem. Soc., 2013, pp. 12122-12134, vol. 135.
Jiang Wu, et al., Copper-Promoted Sandmeyer Difluoromethylthiolation of Aryl and Heteroaryl Diazonium Salts, Angew. Chem. Int. Ed., 2015, pp. 7648-7652, vol. 54.
Matthew A. Larsen, et al., Iridium-Catalyzed C-H Borylation of Heteroarenes: Scope, Regioselectivity, Application to Late-Stage Functionalization, and Mechanism, J. Am. Chem. Soc., 2014, pp. 4287-4299, vol. 136.
Zhi-Yun Liu, et al., B(C6F5)3-Catalyzed Cascade Reduction of Pyridines, Angew. Chem., 2017, pp. 1-5, vol. 129.
Sébastien Alazet, et al., Selective trifluoromethylthiolation of heteroaromatic sp2 C-H bonds with the 2nd generation of trifluoromethanesulfenamide reagent, Journal of Fluorine Chemistry, 2015, pp. 78-81, vol. 171.
M. R. C. Gerstenberger, et al., (Perhalogenemethylthio)-Heterocyclene, XV: Acid And Base Catalyzed Conversions Of Furan, Selenophene And Pyridine, Journal of Fluorine Chemistry, 1983, pp. 525-540, vol. 23.
A. Haas, et al., Perhalogenmethylmercapto-heterocyclen, IX: (Perchlormethylmercapto)-and (Perfluormethylmercapto) Pyridine, Journal of Fluorine Chemistry, 1978, pp. 509-518, vol. 11.
Chaya Pooput, et al., A New and Efficient Method for the Synthesis of Trifluoromethylthio- and Selenoethers, Organic Letters, 2004, pp. 301-303, vol. 6, No. 2.
Iris Kieltsch, et al., Mild Electrophilic Trifluoromethylation of Carbon- and Sulfur-Centered Nucleophiles by a Hypervalent Iodine(III)-CF3 Reagent **, Angew. Chem. Int. Ed., 2007, pp. 754-757, vol. 46.
Vaibhav P. Mehta et al., S , N , and Se-Difluoromethylation Using Sodium Chlorodifluoroacetate, Organic Letters, 2013, pp. 5036-5039, vol. 15, No. 19.
Francois Baert, et al., Electrophilic Trifluoromethanesulfanylation of Organometallic Species with Trifluoromethanesulfanamides **, Angew. Chem. Int. Ed., 2012, pp. 10382-10385, vol. 51.
Georgiy Teverovskiy, et al., Pd-Catalyzed Synthesis of Ar-SCF3 Compounds under Mild Conditions **, Angew. Chem. Int. Ed., 2011, pp. 7312-7314, vol. 50.
Jinyan Yang, et al., Visible-Light Photoredox Difluoromethylation of Phenols and Thiophenols with Commercially Available Difluorobromoacetic Acid, Org. Lett., 2017, pp. 2758-2761, vol. 19.
Jiang Wu, et al., Palladium-catalyzed difluoromethylthiolation of heteroaryl bromides, iodides, triflates and aryl iodides†, Chem. Sci., 2016, pp. 3757-3762, vol. 7.
Yining Ji, et al., Innate C-H trifluoromethylation of heterocycles, PNAS, 2011, pp. 14411-14415, vol. 108, No. 35.
David A. Nagib, et al., Trifluoromethylation of arenes and heteroarenes by means of photoredox catalysis, Nature, 2011, pp. 224-228, vol. 480.

(Continued)

*Primary Examiner* — Timothy R Rozof
(74) *Attorney, Agent, or Firm* — Bayramoglu Law Offices LLC

(57) ABSTRACT

A method for preparing a pyridine compound substituted with trifluoromethylthio, difluoromethylthio or trifluoromethyl in the meta position is provided, which includes S1. in a glove box filled with nitrogen, adding a catalyst, a solvent, pinacolborane, and pyridine to a reaction flask, stirring the mixture, and performing a reaction at 40-100° C. for 2-12 hours to obtain dihydropyridine; S2. adding a trifluoromethylthio reagent, a difluoromethylthio reagent, or a trifluoromethyl reagent to the reaction flask, stirring the mixture, and performing a reaction at room temperature to 80° C. for 2-12 hours to obtain trifluoromethylthio-, difluoromethylthio- or trifluoromethyl-substituted dihydropyridine; and S3. placing the reaction flask in the air or adding 2,3-dichloro-5,6-dicyanobenzoquinone, stirring same, and performing a reaction at room temperature for 4-12 hours, followed by distillation under reduced pressure to remove the solvent and column chromatography separation to obtain the meta-substituted pyridine compound.

9 Claims, No Drawings

(56) References Cited

PUBLICATIONS

Yuta Fujiwara, et al., Practical and innate carbon-hydrogen functionalization of heterocycles, Nature, 2012, pp. 95-99, vol. 492.
Xuan Zhang, et al., Phosphorus-mediated sp2-sp3 couplings for C-H fluoroalkylation of azines, Nature, 2021, pp. 217-222, vol. 594.

* cited by examiner

METHOD FOR PREPARING PYRIDINE COMPOUND SUBSTITUTED WITH TRIFLUOROMETHYLTHIO, DIFLUOROMETHYLTHIO OR TRIFLUOROMETHYL IN META POSITION

CROSS REFERENCE TO THE RELATED APPLICATIONS

This application is a continuation application of International Application No. PCT/CN2022/099346, filed on Jun. 17, 2022, which is based upon and claims priority to Chinese Patent Application No. 202210519999.5, filed on May 12, 2022, the entire contents of which are incorporated herein by reference.

TECHNICAL FIELD

The present application relates to the field of chemical synthesis, and in particular to a method for preparing a pyridine compound substituted with trifluoromethylthio, difluoromethylthio or trifluoromethyl in the meta position.

BACKGROUND

As a dominant group, pyridine structure exists widely in drug molecules. However, due to the relatively high polarity of pyridine structure, drug molecules containing pyridine structure usually have poor lipophicity. Trifluoromethylthio has higher lipophilicity ($\pi$=1.44), so the introduction of trifluoromethylthio into drug molecules containing pyridine structure can effectively regulate the lipid solubility and metabolic stability of the drug molecules; on the other hand, difluoromethylthio contains hydrogen bonds, which can also effectively regulate the chemical properties of the drugs and improve the biological activities thereof. Trifluoromethyl, as a bioisostere of methyl, is one of the most common fluorine-containing functional groups in drug molecules and can enhance the metabolic stability of drug molecules and regulate lipophilicity. Therefore, the development of a direct, efficient and universal method for the trifluoromethylthiolation, difluoromethylthiolation and trifluoromethylation of pyridine has higher application value.

Since pyridine is an electron-deficient aromatic ring and has relatively low electrophilic substitution reaction activity, direct electrophilic trifluoromethylthiolation, difluoromethylthiolation or trifluoromethylation may usually only occur on a pyridine ring with an electron-rich functional group. At present, there are two relatively common methods for introducing trifluoromethylthio or difluoromethylthio into pyridine in the meta position. One of the methods is to react a lithium pyridine reagent with a corresponding strong electrophilic reagent (electrophilic trifluoromethylthiolation or difluoromethylthiolation reagent) to obtain a corresponding product (S. Alazet, L. Zimmer, T. Billard. *J. Fluorine. Chem.* 2015, 171, 78; M. R. C. Gerstenberger, A. Haas. *J. Fluorine. Chem.* 1983, 23, 525; A. Haas, U. Niemann. *J. Fluorine. Chem.* 1978, 11, 509.):

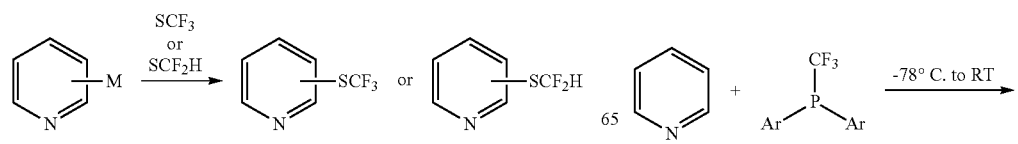

the other one of the methods is a functional group conversion method, i.e., converting another functional group on pyridine into trifluoromethylthio or difluoromethylthio (C. Pooput, M. Medebielle, W. R. Dolbier. *Org. Lett.* 2004, 6, 301; I. Kieltsch, P. Eisenberger, A. Togni. *Angew. Chem. Int. Ed.* 2007, 46, 754; V. P. Mehta, M. F. Greaney. *Org. Lett.* 2013, 15, 5036; F. Baert, J. Colomb, T. Billard. *Angew. Chem. Int. Ed.* 2012, 51, 10382; G. Teverovskiy, D. S. Surry, S. L. Buchwald. *Angew. Chem. Int. Ed.* 2011, 50, 7312; J. Yang, M. Jiang, Y. Jin, H. Yang, H. Fu. *Org. Lett.* 2017, 19, 2758; J. Wu, Y Liu, C. Lua, Q. Shen. *Chem. Sci.* 2016, 7, 3757; J. Wu, Y Gu, X. Leng, Q. Shen. *Angew. Chem. Int. Ed.* 2015, 54, 7648.):

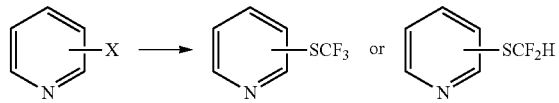

wherein X is SCN, SH, SPy, Cl, Br, I, B(OH)$_2$, BF$_3$K, N$_2^+$, or COOH.

However, the above two methods both have relatively great limitations. For example, in the first method, a relatively strong alkali is usually required to prepare a substrate, so the functional group has relatively poor tolerance and the application scope of the method is limited; and in the second method, it is necessary to functionalize the substrate in advance, which makes it difficult to realize the corresponding transformation for a substrate without the corresponding functional group.

At present, there are two main methods for the direct trifluoromethylation of pyridine. One of the methods is by a free radical reaction (Y. Ji, T. Brueckl, R. D. Baxter, Y. Fujiwara, I. B. Seiple, S. Su, D. G. Blackmond, P. S. Baran. *Proc. Natl. Acad. Sci. U.S.A.* 2011, 108, 14411; D. A. Nagib, D. W. C. MacMillan. *Nature* 2011, 480, 224; Y. Fujiwara, J. A. Dixon, F. O'Hara, E. D. Funder, D. D. Dixon, R. A. Rodriguez, R. D. Baxter, B. Herlé, N. Sach, M. R. Collins, Y. Ishihara, P. S. Baran. *Nature* 2012, 492, 95; F. O'Hara, D. G. Blackmond, P. S. Baran. *J. Am. Chem. Soc.* 2013, 135, 12122):

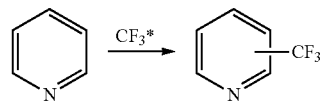

the other one is to realize trifluoromethylation of pyridine in the para position by coupling with an organic phosphine ligand (X. Zhang, K. G. Nottingham, C. Patel, J. V. Alegre-Requena, J. N. Levy, R. S. Paton, A. McNally. *Nature* 2021, 594, 217.):

-continued

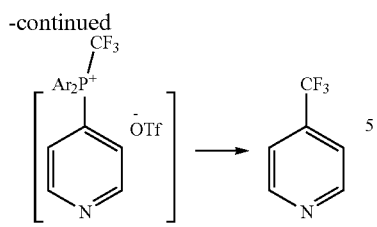

The main problems of the above two methods are as follows: the first method usually obtains mixed products resulting from the trifluoromethylation of pyridine in different positions, that is, the regioselectivity of the reaction is not good; and the second method needs to be carried out at a harsher temperature such as at −78° C. and realizes introduction of trifluoromethyl into pyridine in the para position.

SUMMARY

An object of the present application is to provide a method for preparing a pyridine compound substituted with trifluoromethylthio, difluoromethylthio or trifluoromethyl in the meta position. The method has high functional group compatibility, no need for pre-functionalization, mild reaction conditions, easy scale-up production, and also relatively good chemical selectivity and regioselectivity.

To this end, the following technical solution is used in the present application:

A method for preparing a pyridine compound substituted with trifluoromethylthio, difluoromethylthio or trifluoromethyl in the meta position, comprising the following steps:

S1. preparation of 1,4-dihydropyridine or 1,2-dihydropyridine:

in a glove box filled with nitrogen, adding a catalyst, a solvent, pinacolborane, and pyridine to a reaction flask, and stirring the mixture for a sufficient reaction to obtain dihydropyridine, with the reaction formula being as follows:

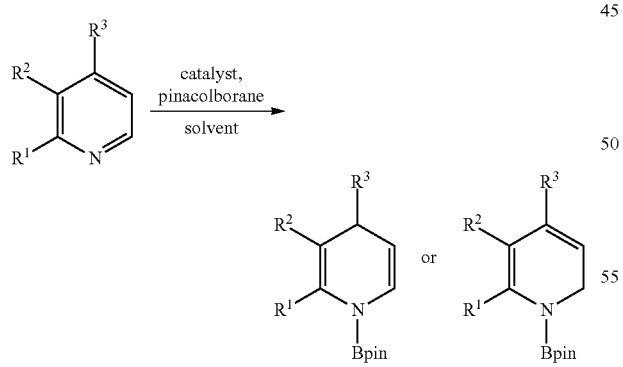

wherein:
the catalyst is triarylboron, the molar ratio of the triarylboron to the pyridine is (5-10): 100, and the structural formula of the triarylboron is $B(R^4)_3$ in which $R^4$ is phenyl, pentafluorophenyl, 3,5-bis(trifluoromethyl)-substituted phenyl, or 2,4,6-trifluoro-substituted phenyl;

the equivalent ratio of the pinacolborane to the pyridine is 1.1:1;

the solvent is tetrahydrofuran, dichloromethane, dioxane, 1,2-dichloroethane, or an aromatic solvent; and the reaction temperature is 40-100° C. and the reaction time is 2-12 hours;

S2. electrophilic substitution reaction of dihydropyridine:

adding a trifluoromethylthio reagent, a difluoromethylthio reagent, or a trifluoromethyl reagent to the reaction flask, and stirring the mixture in a nitrogen atmosphere until the reaction is complete, so as to obtain dihydropyridine substituted with trifluoromethylthio, difluoromethylthio or trifluoromethyl in the meta position, with the reaction formula being as follows:

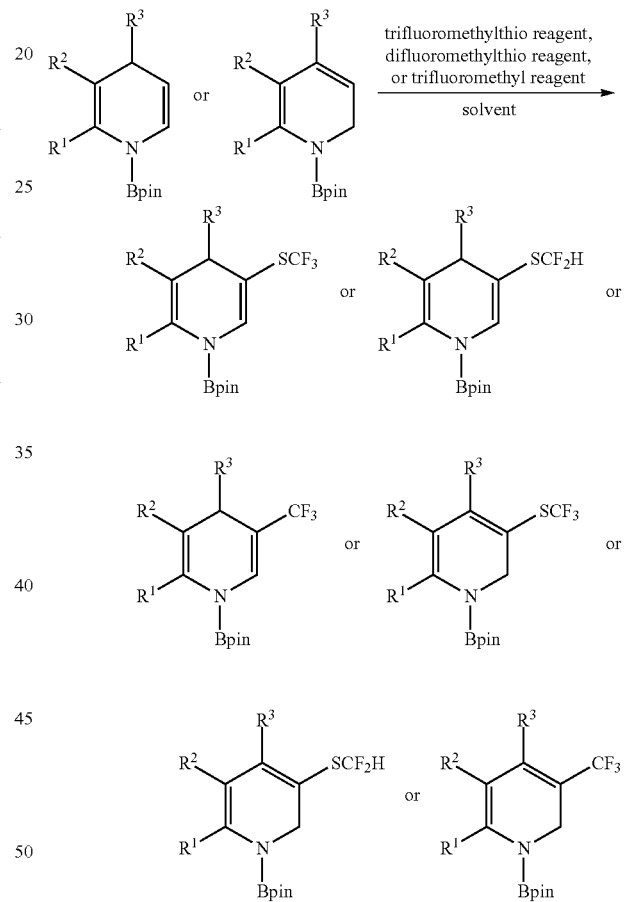

wherein the reaction temperature is room temperature to 80° C., and the reaction time is 2 to 12 hours; and S3. oxidative aromatization to obtain the pyridine compound substituted with trifluoromethylthio, difluoromethylthio or trifluoromethyl in the meta position:

placing the reaction flask in the air or adding 2,3-dichloro-5,6-dicyanobenzoquinone, stirring until the reaction is complete, performing distillation under reduced pressure to remove the solvent, and then performing column chromatography separation to obtain the pyridine compound substituted with trifluoromethylthio, difluoromethylthio or trifluoromethyl in the meta position, with the reaction formula being as follows:

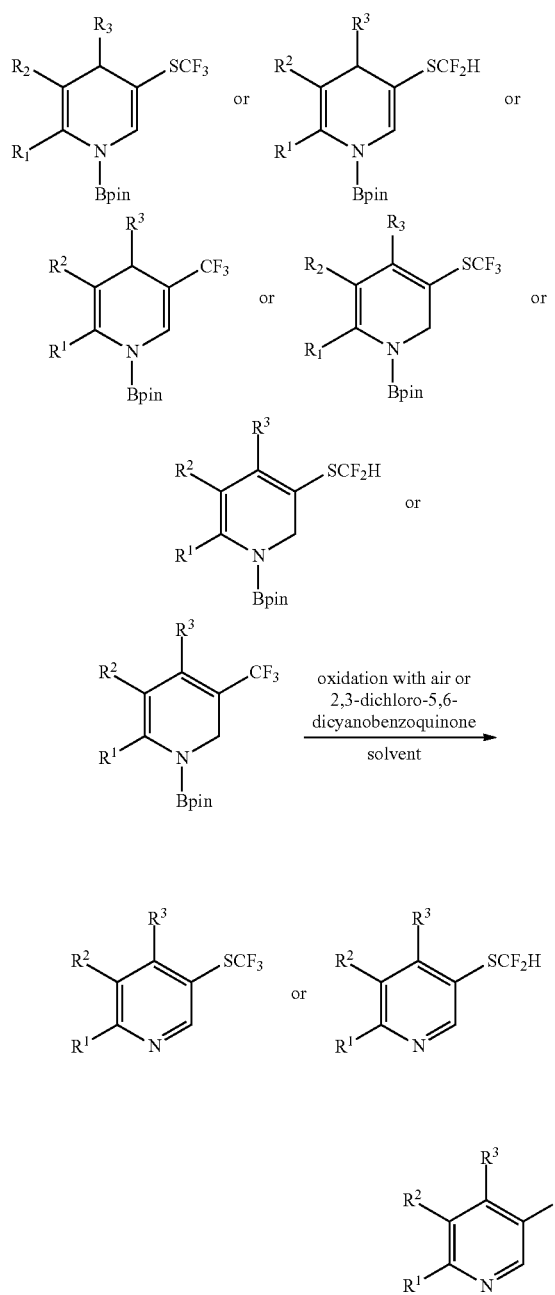

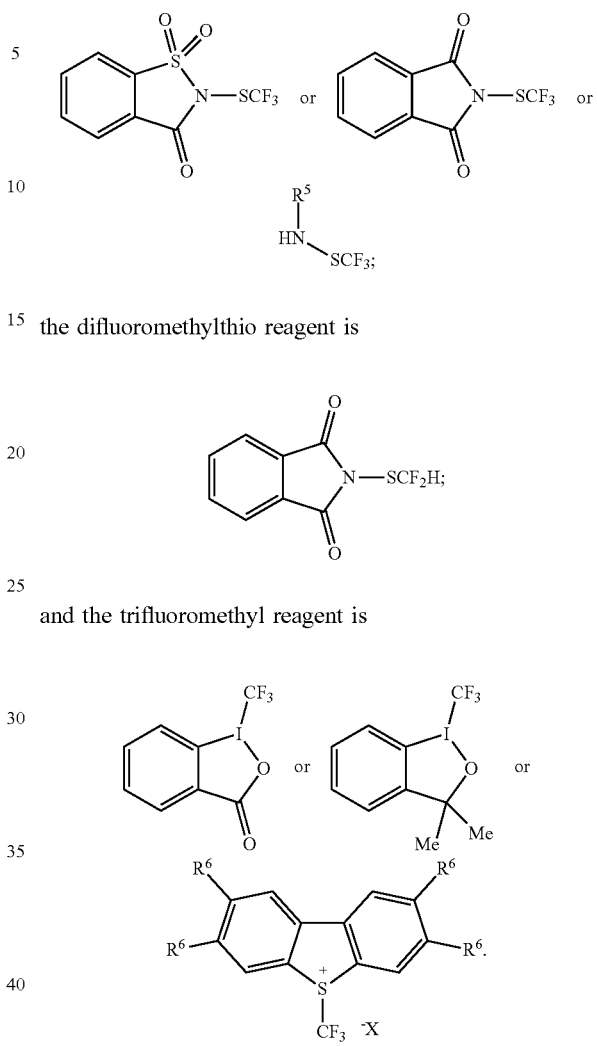

wherein:

the equivalent ratio of the 2,3-dichloro-5,6-dicyanobenzoquinone to the pyridine is 1.5:1;

the reaction temperature is room temperature, and the reaction time is 4 to 12 hours; and in the structural formulas of the pyridine, dihydropyridine, and pyridine compound substituted with trifluoromethylthio, difluoromethylthio or trifluoromethyl in the meta position, $R^1$ is hydrogen, alkyl, aryl, substituted aryl, or heteroaryl substituent; $R^2$ is hydrogen, alkyl, halogen, amino, ether group, ester group, aryl, substituted aryl, or heteroaryl substituent; and $R^3$ is hydrogen, alkyl, aryl, substituted aryl, or heteroaryl substituent.

Preferably, in step S2, the trifluoromethylthio reagent is:

the difluoromethylthio reagent is and the trifluoromethyl reagent is

Preferably, in the above structural formula, $X^-$ is $BF_4^-$, $TfO^-$, $Cl^-$, $Br^-$, or $I^-$; $R^5$ is aryl or substituted aryl; and $R^6$ is hydrogen or fluorine.

When $R^1$ is heteroaryl, the heteroaryl is preferably furyl or thienyl.

When $R^2$ is heteroaryl, the heteroaryl is preferably furyl, thienyl, or pyridyl.

When $R^2$ is halogen, the halogen is chlorine, bromine, or iodine.

When $R^3$ is heteroaryl, the heteroaryl is furyl, thienyl, or pyridyl.

In the present application, with a boron Lewis acid as a catalyst, by using the strategy of dearomatization-rearomatization of pyridine, trifluoromethylthiolation, difluoromethylthiolation or trifluoromethylation of pyridine in the meta position are realized, wherein: firstly, under catalysis by the boron Lewis acid, pyridine reacts with pinacolborane to generate electron-rich 1,4-dihydropyridine or 1,2-dihydropyridine, which easily reacts with an electrophilic trifluoromethylthio, difluoromethylthio or trifluoromethyl reagent; in the second step, trifluoromethylthiolation, difluoromethylthiolation or trifluoromethylation of dihydropyridine occurs; and finally, oxidative rearomatization is performed to obtain pyridine products substituted with trifluoromethylthio, difluoromethylthio and trifluoromethyl in the meta position.

Compared with the prior art, the present application has the following beneficial effects:
1. In the present application, there is no need to use a relatively expensive metal reagent; instead, a boron Lewis acid is used as a catalyst, which is not only beneficial to environmental protection, but also reduces the production cost and has easy scale up production;
2. in the present application, the trifluoromethylthio, difluoromethylthio or trifluoromethyl substitution reaction only occurs in the meta position of pyridine, but not in the ortho position and para position of the pyridine nor in other aromatic rings, and the reaction has relatively good chemical selectivity and regioselectivity;
3. in the present application, the reaction takes place under relatively mild conditions, and the reaction can produce a product at room temperature to 80° C.;
4. the product obtained by the present application is easily further converted into sulfone and sulfoxide products, so it is widely used in medicine, pesticides, material sciences, etc.;
5. the substrate of the present application has a wide application range, has relatively high reaction activity for all of the ortho-, meta- and para-monosubstitution or polysubstitution of pyridine, and also has relatively good applicability for the late functionalization modification of drug molecules containing pyridine structure and can be applied to drug research, development and production;
6. the present application has strong functional group compatibility, and the substituent can be alkyl, halogen, amino, ether group, ester group, aryl, substituted aryl, heteroaryl substituent, etc.; and
7. the present application can be scaled up to a gram scale and can remain a relatively high yield when the dosage of the catalyst is reduced to 5 mol %, and by-products can be recovered and reused, thereby reducing the production cost and having better green chemical properties.

DETAILED DESCRIPTION OF THE EMBODIMENTS

The method of the present application will be illustrated in detail in conjunction with specific examples.

In the reaction formulas of the following examples, LA is a catalyst; HBpin is pinacolborane; THF is tetrahydrofuran; DCM is dichloromethane; toluene is methylbenzene; and equiv is equivalent.

Example 1

A method for preparing 3-phenyl-5-trifluoromethylthiopyridine, comprising the following steps:
S1. preparation of dihydropyridine by a hydroboration reaction, wherein in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 3-phenylpyridine (1a) were added to an 8 mL small reaction flask, and the mixture was stirred and reacted at 80° C. for 5 hours to obtain 3-phenyl-1-(4,4,5,5-tetramethyl-1,3,2-dioxaborolane)-1,4-dihydropyridine, with the reaction formula being as follows:

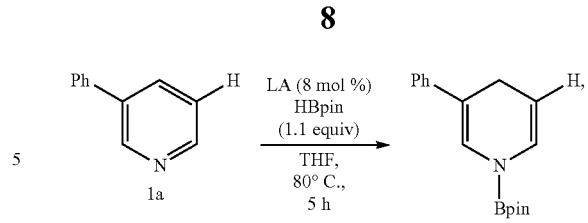

wherein the catalyst LA was B(2,4,6-$F_3C_6H_2$)$_3$, and the structural formula thereof was as follows:

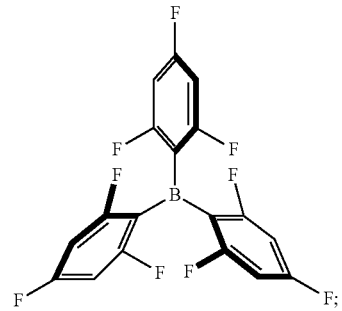

S2. electrophilic substitution reaction of dihydropyridine, wherein the system was cooled to room temperature, and 62.3 mg (0.22 mmol, 1.1 equiv) of N-trifluoromethylthiosaccharin (2a) was added to the above small reaction flask and reacted at 80° C. for 2 hours to produce 3-phenyl-1-(4,4,5,5-tetramethyl-1,3,2-dioxaborolane)-5-trifluoromethylthio-1,4-dihydropyridine, with the reaction formula being as follows:

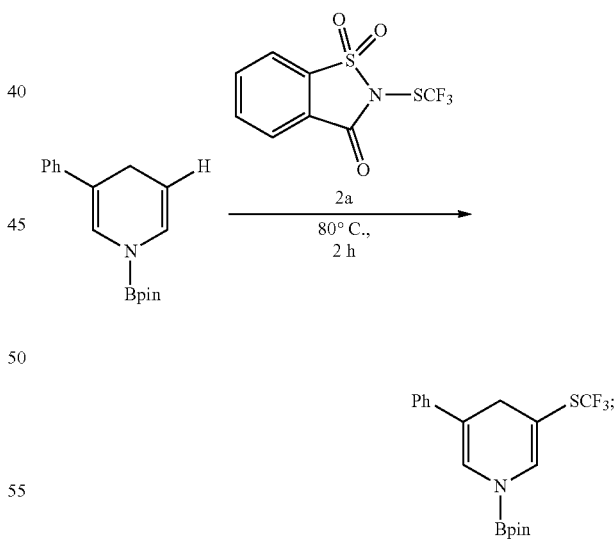

and

S3. oxidative aromatization to obtain a meta-substituted pyridine compound, wherein the system was cooled to room temperature, the small reaction flask was removed from the glove box, and the system was stirred in the air for 4 hours to produce 3-phenyl-5-trifluoromethylthiopyridine (3a), with the reaction formula being as follows:

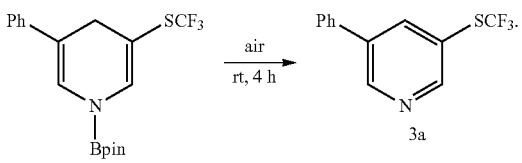

After the reaction was complete, the solvent was removed by rotary evaporation, and the residue was separated and purified by silica gel column chromatography to obtain the product 3-phenyl-5-trifluoromethylthiopyridine as a colorless oil with a yield of 94%.

The product was characterized as follows:

$^1$H NMR (400 MHz, CDCl$_3$) δ 8.94 (s, 1H), 8.81 (s, 1H), 8.16 (s, 1H), 7.61-7.57 (m, 2H), 7.54-7.49 (m, 2H), 7.48-7.43 (m, 1H). 13C NMR (101 MHz, CDCl$_3$) δ 154.0, 150.2, 141.8, 137.7, 136.1, 129.4, 129.2 (q, J=308.8 Hz, SCF$_3$), 128.9, 127.3, 122.1 (q, J=1.5 Hz). $^{19}$F NMR (376 MHz, CDCl$_3$) δ −42.14 (s, SCF$_3$). HRMS (ESI) calcd. for C$_{12}$H$_9$F$_3$NS+(M+H)$^+$: 256.0402, Found: 256.0402.

Example 2

A method for preparing 4-phenyl-3-trifluoromethylthiopyridine, comprising the following steps:

S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 4-phenylpyridine (1b) were added to an 8 mL small reaction flask, and the mixture was stirred and reacted at 80° C. for 12 hours to obtain 4-phenyl-1-(4,4,5,5-tetramethyl-1,3,2-dioxaborolane)-1,2-dihydropyridine, with the reaction formula being as follows:

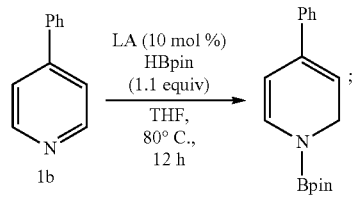

wherein the catalyst LA was the same as in Example 1, i.e., B(2,4,6-F$_3$C$_6$H$_2$)$_3$;

S2. the system was cooled to room temperature, and 62.3 mg (0.22 mmol, 1.1 equiv) of N-trifluoromethylthiosaccharin (2a) was added to the above small reaction flask and reacted at room temperature for 12 hours to produce 4-phenyl-1-(4,4,5,5-tetramethyl-1,3,2-dioxaborolane)-3-trifluoromethylthio-1,2-dihydropyridine, with the reaction formula being as follows:

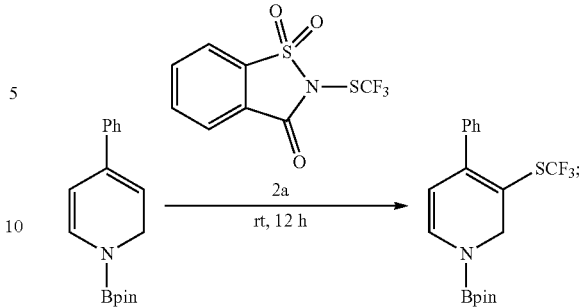

and

S3. the system was cooled to room temperature, the small reaction flask was removed from the glove box, and the system was stirred in the air for 4 hours to produce 4-phenyl-3-trifluoromethylthiopyridine (3b), with the reaction formula being as follows:

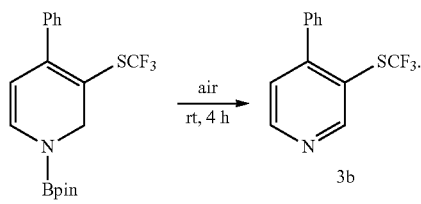

After the reaction was complete, the solvent was removed by rotary evaporation, and the residue was separated and purified by silica gel column chromatography to obtain the product 4-phenyl-3-trifluoromethylthiopyridine as a white solid with a yield of 56%.

The product was characterized as follows:

$^1$H NMR (400 MHz, CDCl$_3$) δ 8.96 (s, 1H), 8.72 (d, J=5.0 Hz, 1H), 7.50-7.43 (m, 3H), 7.38 (d, J=5.0 Hz, 1H), 7.36-7.33 (m, 2H). $^{13}$C NMR (101 MHz, CDCl$_3$) δ 157.2, 155.5, 151.6, 137.5, 129.2, 129.1 (q, J=309.3 Hz, SCF$_3$), 128.9, 128.4, 125.5, 120.5 (q, J=2.0 Hz). 19F NMR (376 MHz, CDCl$_3$) δ −41.83 (s, SCF$_3$). HRMS (ESI) calcd. for C$_{12}$H$_9$F$_3$NS+(M+H)$^+$: 256.0402, Found: 256.0400.

Example 3

A method for preparing 2-phenyl-3,5-bis(trifluoromethylthio)pyridine, comprising the following steps:

S1. in a glove box filled with nitrogen, 13 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 2-phenylpyridine (1c) were added to an 8 mL small reaction flask, and the mixture was stirred and reacted at 40° C. for 2 hours to obtain 2-phenyl-1-(4,4,5,5-tetramethyl-1,3,2-dioxaborolane)-1,4-dihydropyridine, with the reaction formula being as follows:

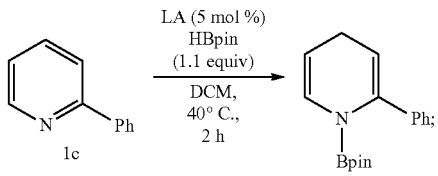

wherein the catalyst LA was B(3,5-(CF$_3$)$_2$C$_6$H$_3$)$_3$, and the structural formula thereof was as follows:

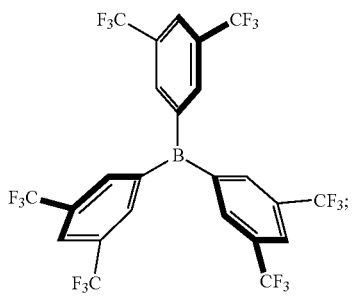

S2. the system was cooled to room temperature, and 124.6 mg (0.44 mmol, 2.2 equiv) of N-trifluoromethylthiosaccharin (2a) was added to the above small reaction flask and reacted at 40° C. for 3 hours to produce 2-phenyl-1-(4,4,5,5-tetramethyl-1,3,2-dioxaborolane)-3,5-bis(trifluoromethylthio)-1,4-dihydropyridine, with the reaction formula being as follows:

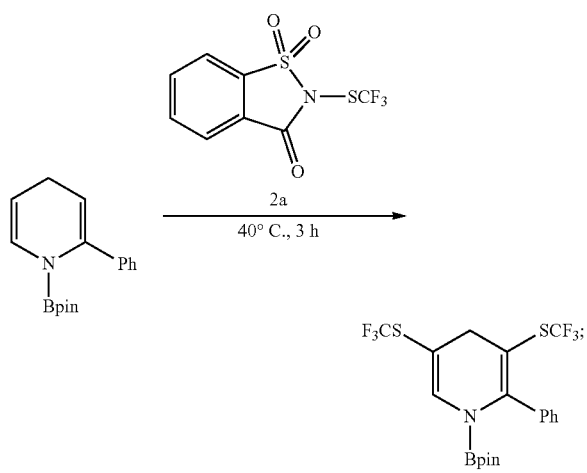

and

S3. the system was cooled to room temperature, the small reaction flask was removed from the glove box, 68.1 mg (0.3 mmol, 1.5 equiv) of 2,3-dichloro-5,6-dicyanobenzoquinone was added, and the mixture was stirred in the air for 4 hours to produce 2-phenyl-3,5-bis(trifluoromethylthio)pyridine (3c), with the reaction formula being as follows:

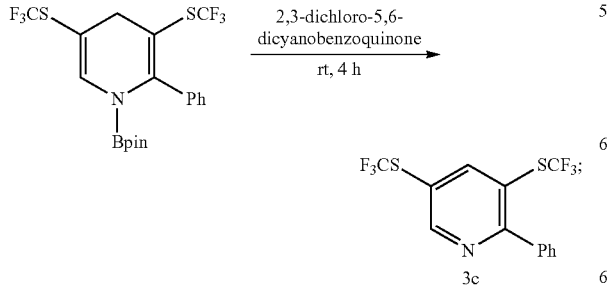

after the reaction was complete, the solvent was removed by rotary evaporation, and the residue was separated and purified by silica gel column chromatography to obtain the product 2-phenyl-3,5-bis(trifluoromethylthio)pyridine as a colorless oil with a yield of 68%.

The product was characterized as follows:

$^1$H NMR (400 MHz, CDCl$_3$) δ 8.94 (d, J=1.7 Hz, 1H), 8.41 (s, 1H), 7.65-7.56 (m, 2H), 7.55-7.48 (m, 3H). $^{13}$C NMR (101 MHz, CDCl$_3$) δ 165.0, 156.3, 151.3, 137.7, 129.8, 129.7, 128.9 (q, J=309.2 Hz, SCF$_3$), 128.9 (q, J=309.9 Hz, SCF$_3$), 128.4, 121.9 (q, J=1.7 Hz), 121.0 (q, J=2.0 Hz). $^{19}$F NMR (376 MHz, CDCl$_3$) δ −41.45 (s, SCF$_3$), −42.04 (s, SCF$_3$). HRMS (ESI) calcd. for C$_{13}$H$_8$F$_6$NS$_2^+$ (M+H)$^+$: 355.9997, Found: 355.9993.

Example 4

A method for preparing methyl 6-methyl-5-trifluoromethylthionicotinate, comprising the following steps:

S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 30.2 mg (0.2 mmol, 1.0 equiv) of methyl 6-methylnicotinate (1d) were added to an 8 mL small reaction flask, and the mixture was stirred and reacted at 40° C. for 4 hours to obtain methyl 6-methyl-1-(4,4,5,5-tetramethyl-1,3,2-dioxaborolane)-1,4-dihydropyridine-3-carboxylate, with the reaction formula being as follows:

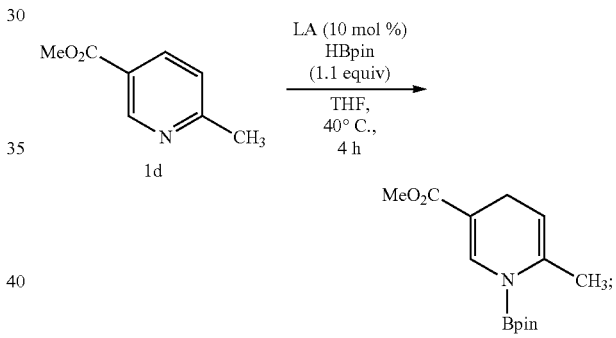

wherein the catalyst LA was the same as in Example 1, i.e., B(2,4,6-F$_3$C$_6$H$_2$)$_3$;

S2. the system was cooled to room temperature, and 62.3 mg (0.22 mmol, 1.1 equiv) of N-trifluoromethylthiosaccharin (2a) was added to the above small reaction flask and reacted at room temperature for 12 hours to produce methyl 6-methyl-1-(4,4,5,5-tetramethyl-1,3,2-dioxaborolane)-5-trifluoromethylthio-1,4-dihydropyridine-3-carboxylate, with the reaction formula being as follows:

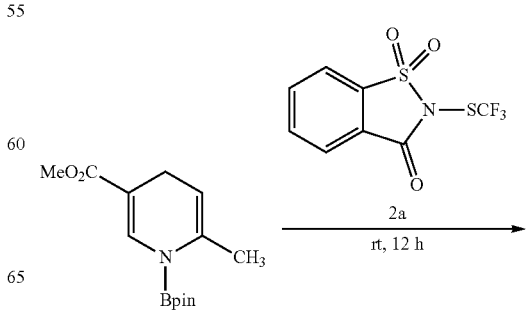

and

S3. the system was cooled to room temperature, the small reaction flask was removed from the glove box, and the system was stirred in the air for 12 hours to produce methyl 6-methyl-5-trifluoromethylthionicotinate (3d), with the reaction formula being as follows:

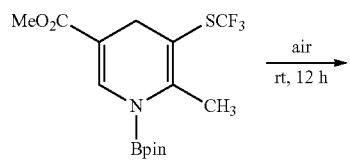

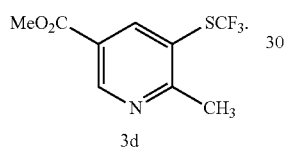

After the reaction was complete, the solvent was removed by rotary evaporation, and the residue was separated and purified by silica gel column chromatography to obtain the product methyl 6-methyl-5-trifluoromethylthionicotinate as a white solid with a yield of 56%.

The product was characterized as follows:

$^1$H NMR (400 MHz, CDCl$_3$) δ 9.16 (d, J=1.7 Hz, 1H), 8.53 (d, J=1.7 Hz, 1H), 3.96 (s, 3H), 2.85 (s, 3H). $^{13}$C NMR (101 MHz, CDCl$_3$) δ 168.0, 164.7, 152.2, 146.4, 129.3 (q, J=311.1 Hz, SCF$_3$), 125.0, 121.0 (q, J=2.0 Hz), 52.75, 24.2. $^{19}$F NMR (376 MHz, CDCl$_3$) δ −41.78 (s, SCF$_3$). HRMS (ESI) calcd. for C$_9$H$_9$F$_3$NO$_2$S$^+$ (M+H)$^+$: 252.0301, Found: 252.0297.

Example 5

A method for preparing 5-chloro-6'-methyl-3-methylsulfonyl-5-trifluoromethylthio-2,3'-bipyridine, comprising the following steps:

S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 71.8 mg (0.2 mmol, 1.0 equiv) of etoricoxib (1e) were added to an 8 mL small reaction flask, and the mixture was stirred and reacted at 80° C. for 8 hours to obtain 5-chloro-6'-methyl-3-(4-(methylsulfonyl)phenyl)-1'-(4,4,5,5-tetramethyl-1,3,2-dioxaborolane)-1',4'-dihydro-2,3'-bipyridine, with the reaction formula being as follows:

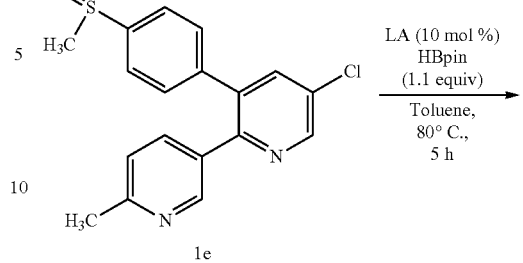

wherein the catalyst LA was the same as in Example 1, i.e., B(2,4,6-F$_3$C$_6$H$_2$)$_3$;

S2. the system was cooled to room temperature, and 62.3 mg (0.22 mmol, 1.1 equiv) of N-trifluoromethylthiosaccharin (2a) was added to the above small reaction flask and reacted at 80° C. for 4 hours to obtain 5-chloro-6'-methyl-3-(4-(methylsulfonyl)phenyl)-1'-(4,4,5,5-tetramethyl-1,3,2-dioxaborolane)-5'-trifluoromethylthio-1',4'-dihydro-2,3'-bipyridine, with the reaction formula being as follows:

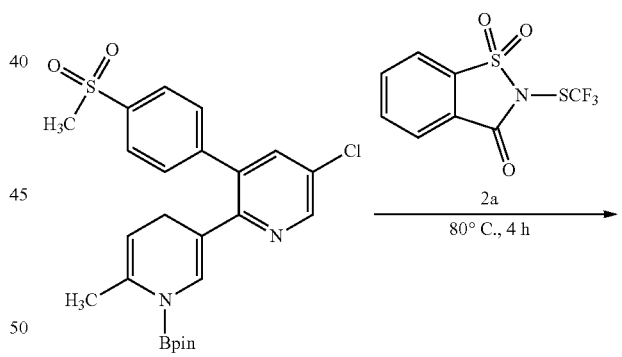

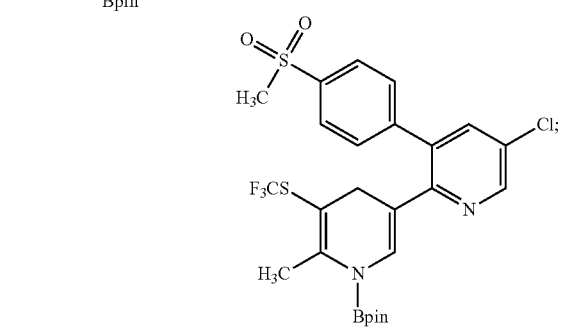

and

S3. the system was cooled to room temperature, the small reaction flask was removed from the glove box, and the system was stirred in the air for 4 hours to produce 5-chloro-6'-methyl-3-(4-(methylsulfonyl)phenyl)-5'((trifluoromethyl)thio)-2,3'-bipyridine (3e), with the reaction formula being as follows:

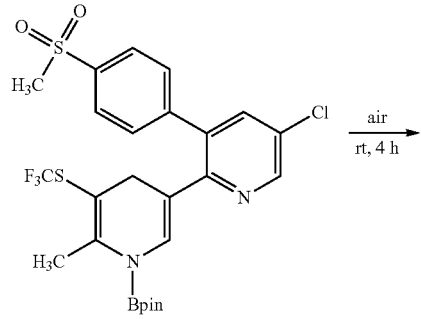

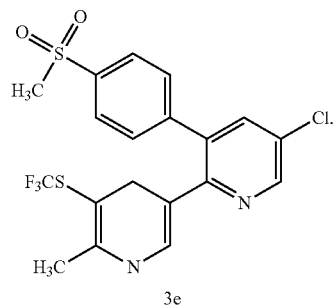

After the reaction was complete, the solvent was removed by rotary evaporation, and the residue was separated and purified by silica gel column chromatography to obtain the product 5-chloro-6'-methyl-3-methylsulfonyl-5-trifluoromethylthio-2,3'-bipyridine as a white solid with a yield of 65%.

The product was characterized as follows:

$^1$H NMR (400 MHz, CDCl$_3$) δ 8.73 (d, J=1.7 Hz, 1H), 8.66 (d, J=1.7 Hz, 1H), 7.93 (d, J=8.1 Hz, 2H), 7.77-7.74 (m, 2H), 7.40 (d, J=8.1 Hz, 2H), 3.06 (s, 3H), 2.75 (s, 3H). $^{13}$C NMR (101 MHz, CDCl$_3$) δ 163.2, 151.9, 150.5, 148.7, 146.1, 143.1, 140.6, 138.2, 135.7, 132.9, 131.8, 130.3, 129.2 (q, J=309.3 Hz, SCF$_3$), 128.3, 112.0 (d, J=1.8 Hz), 44.41, 23.67. $^{19}$F NMR (376 MHz, CDCl$_3$) δ −41.82 (s, SCF$_3$). HRMS (ESI) calcd. for C$_{19}$H$_{15}$ClF$_3$N$_2$O$_2$S$_2{}^+$ (M+H)$^+$: 459.0210, Found: 459.0208.

Example 6

A method for preparing N,N-diethyl-5-trifluoromethylthionicotinamide, comprising the following steps:

S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 35.6 mg (0.2 mmol, 1.0 equiv) of nicotinoyl diethylamine (1f) were added to an 8 mL small reaction flask, and the mixture was stirred and reacted at 80° C. for 8 hours to obtain NA-diethyl-1-(4,4,5,5-tetramethyl-1,3,2-dioxaborolane)-1,4-dihydropyridine-3-carboxamide, with the reaction formula being as follows:

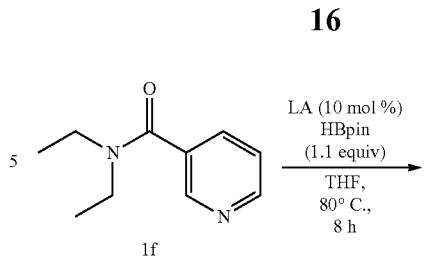

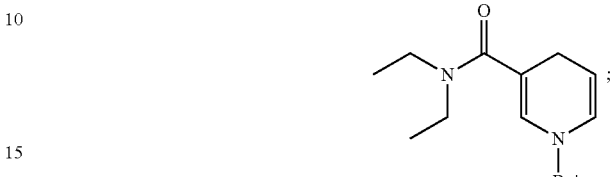

wherein the catalyst LA was the same as in Example 1, i.e., B(2,4,6-F$_3$C$_6$H$_2$)$_3$;

S2. the system was cooled to room temperature, and 62.3 mg (0.22 mmol, 1.1 equiv) of N-trifluoromethylthiosaccharin (2a) was added to the above small reaction flask and reacted at 80° C. for 4 hours to produce NA-diethyl-1-(4,4,5,5-tetramethyl-1,3,2-dioxaborolane)-5-trifluoromethylthio-1,4-dihydropyridine-3-carboxamide, with the reaction formula being as follows:

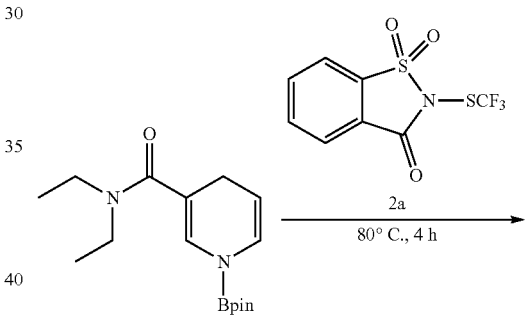

and

S3. the system was cooled to room temperature, the small reaction flask was removed from the glove box, and the system was stirred in the air for 12 hours to produce NA-diethyl-5-trifluoromethylthionicotinamide (3f), with the reaction formula being as follows:

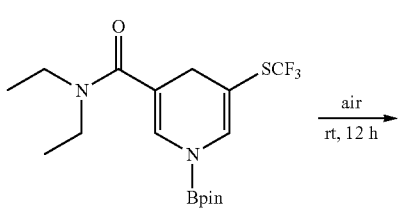

-continued

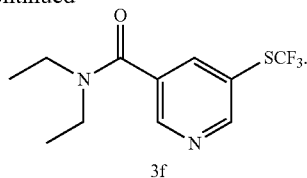
3f

After the reaction was complete, the solvent was removed by rotary evaporation, and the residue was separated and purified by silica gel column chromatography to obtain the product N,N-diethyl-5-trifluoromethylthionicotinamide as a colorless oil with a yield of 76%.

The product was characterized as follows:
$^1$H NMR (400 MHz, CDCl$_3$) δ 8.85 (s, 1H), 8.74 (s, 1H), 8.01 (s, 1H), 3.56 (q, J=6.7 Hz, 2H), 3.25 (q, J=6.7 Hz, 2H), 1.27 (t, J=6.5 Hz, 3H), 1.15 (t, J=6.5 Hz, 3H). $^{13}$C NMR (101 MHz, CDCl$_3$) δ 166.9, 156.0, 149.4, 141.6, 133.8, 129.0 (q, J=309.2 Hz, SCF$_3$), 122.1 (q, J=2.0 Hz), 43.6, 39.9, 14.3, 12.9. $^{19}$F NMR (376 MHz, CDCl$_3$) δ −42.06 (s, SCF$_3$). HRMS (ESI) calcd. for C$_{11}$H$_{14}$F$_3$N$_2$OS$^+$ (M+H)$^+$: 279.0773, Found: 279.0774.

Example 7

A method for preparing 3-difluoromethylthio-5-phenylpyridine, comprising the following steps:
S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 3-phenylpyridine (1a) were added to an 8 mL small reaction flask, and the mixture was stirred and reacted at 80° C. for 5 hours to obtain 3-phenyl-1-(4,4,5,5-tetramethyl-1,3,2-dioxaborolane)-1,4-dihydropyridine, with the reaction formula being as follows:

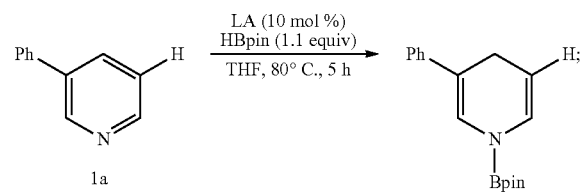

wherein the catalyst LA was the same as in Example 1, i.e., B(2,4,6-F$_3$C$_6$H$_2$)$_3$;
S2. the system was cooled to room temperature, and 50.4 mg (0.22 mmol, 1.1 equiv) of 2-(difluoromethylthio) isoindole-1,3-dione (2b) was added to the above small reaction flask and reacted at 80° C. for 6 hours to produce 3-difluoromethylthio-1-(4,4,5,5-tetramethyl-1,3,2-dioxaborolane)-5-phenyl-1,4-dihydropyridine, with the reaction formula being as follows:

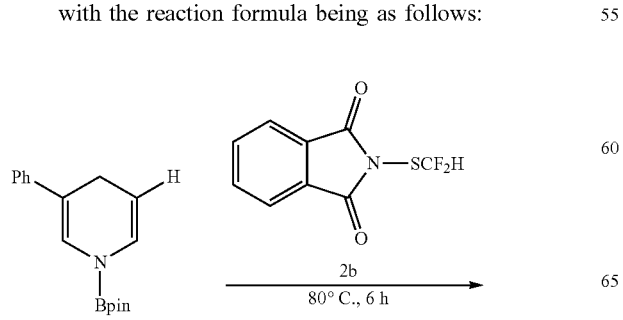

and
S3. the system was cooled to room temperature, the small reaction flask was removed from the glove box, and the system was stirred in the air for 4 hours to produce 3-difluoromethylthio-5-phenylpyridine (3g), with the reaction formula being as follows:

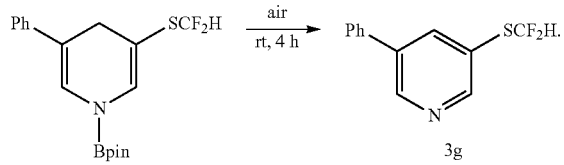

After the reaction was complete, the solvent was removed by rotary evaporation, and the residue was separated and purified by silica gel column chromatography to obtain the product 3-difluoromethylthio-5-phenylpyridine as a colorless oil with a yield of 82%.

The product was characterized as follows:
$^1$H NMR (400 MHz, CDCl$_3$) δ 8.89 (d, J=1.8 Hz, 1H), 8.75 (d, J=1.8 Hz, 1H), 8.10 (t, J=1.8 Hz, 1H), 7.61-7.57 (m, 2H), 7.54-7.48 (m, 2H), 7.47-7.42 (m, 1H), 6.89 (t, J=56.3 Hz, 1H, SCF$_2$H). $^{13}$C NMR (101 MHz, CDCl$_3$) δ 153.5, 149.3, 141.2, 137.4, 136.4, 129.3, 128.8, 127.3, 123.1 (t, J=2.7 Hz), 119.8 (t, J=278.8 Hz, SCF$_2$H). $^{19}$F NMR (376 MHz, CDCl$_3$) δ −91.17 (d, J=56.5 Hz, SCF$_2$H). HRMS (ESI) calcd. for C$_{12}$H$_{10}$F$_2$NS$^+$ (M+H)$^+$: 238.0497, Found: 238.0494.

Example 8

A method for preparing 3-difluoromethylthio-4-phenylpyridine, comprising the following steps:
S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 4-phenylpyridine (1a) were added to an 8 mL small reaction flask, and the mixture was stirred and reacted at 80° C. for 12 hours to obtain 4-phenyl-1-(4,4,5,5-tetramethyl-1,3,2-dioxaborolane)-1,2-dihydropyridine, with the reaction formula being as follows:

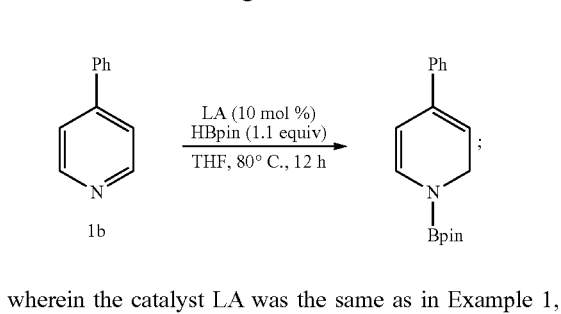

wherein the catalyst LA was the same as in Example 1, i.e., B(2,4,6-F$_3$C$_6$H$_2$)$_3$;

S2. the system was cooled to room temperature, and 50.4 mg (0.22 mmol, 1.1 equiv) of 2-(difluoromethylthio)isoindole-1,3-dione (2b) was added to the above small reaction flask and reacted at 80° C. for 6 hours to obtain 3-difluoromethylthio-1-(4,4,5,5-tetramethyl-1,3,2-dioxaborolane)-4-phenyl-1,2-dihydropyridine, with the reaction formula being as follows:

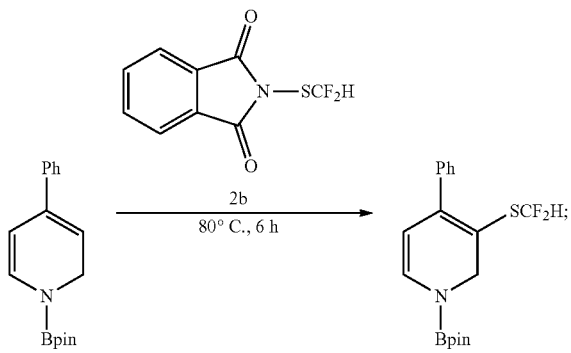

and

S3. the system was cooled to room temperature, the small reaction flask was removed from the glove box, and the system was stirred in the air for 4 hours to produce 3-difluoromethylthio-4-phenylpyridine (3h), with the reaction formula being as follows:

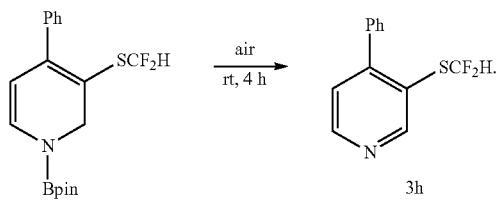

After the reaction was complete, the solvent was removed by rotary evaporation, and the residue was separated and purified by silica gel column chromatography to obtain the product 3-difluoromethylthio-4-phenylpyridine as a white solid with a yield of 50%.

The product was characterized as follows:
$^1$H NMR (400 MHz, CDCl$_3$) δ 8.88 (s, 1H), 8.66 (d, J=5.0 Hz, 1H), 7.49-7.44 (m, 3H), 7.40-7.36 (m, 2H), 7.34 (d, J=5.0 Hz, 1H), 6.64 (t, J=56.4 Hz, 1H, SCF$_2$H). $^{13}$C NMR (101 MHz, CDCl$_3$) δ 156.0, 154.4, 150.7, 137.7, 129.2, 128.9, 128.4, 125.3, 122.0 (t, J=2.6 Hz), 119.8 (t, J=277.1 Hz, SCF$_2$H). $^{19}$F NMR (376 MHz, CDCl$_3$) δ -91.25 (d, J=56.3 Hz, SCF$_2$H). HRMS (ESI) calcd. for C$_{12}$H$_{10}$F$_2$NS$^+$ (M+H)$^+$: 238.0497, Found: 238.0495.

Example 9

A method for preparing 3-phenyl-5-trifluoromethylpyridine, comprising the following steps:
S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 31.0 mg (0.2 mmol, 1.0 equiv) of 3-phenylpyridine (1a) were added to an 8 mL small reaction flask in this order, and the mixture was stirred and reacted at 80° C. for 5 hours to obtain 3-phenyl-1-(4, 4,5,5-tetramethyl-1,3,2-dioxaborolane)-1,4-dihydropyridine, with the reaction formula being as follows:

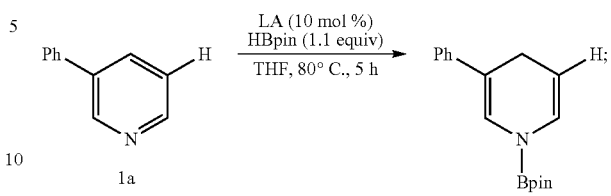

wherein the catalyst LA was the same as in Example 1, i.e., B(2,4,6-F$_3$C$_6$H$_2$)$_3$;
S2. the system was cooled to room temperature, and 69.5 mg (0.22 mmol, 1.1 equiv) of 1-trifluoromethyl-1,2-benziodoxol-3(1H)-one (2c) was added to the above small reaction flask and reacted at room temperature for 1 hours to obtain 3-phenyl-1-(4,4,5,5-tetramethyl-1,3, 2-dioxaborolane)-5-trifluoromethyl-1,4-dihydropyridine, with the reaction formula being as follows:

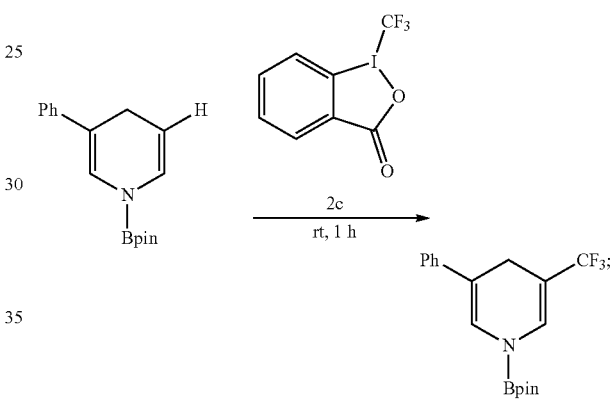

and
S3. the system was cooled to room temperature, the small reaction flask was removed from the glove box, 68.1 mg (0.3 mmol, 1.5 equiv) of 2,3-dichloro-5,6-dicyanobenzoquinone was added, and the mixture was stirred in the air for 4 hours to produce 3-phenyl-5-(trifluoromethyl)pyridine (3i), with the reaction formula being as follows:

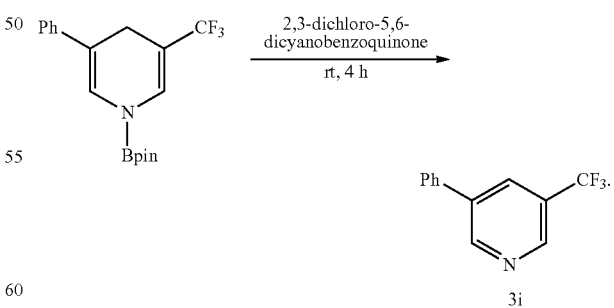

After the reaction was complete, the solvent was removed by rotary evaporation, and the residue was separated and purified by silica gel column chromatography to obtain the product 3-phenyl-5-trifluoromethylpyridine as a white solid with a yield of 48%.

The product was characterized as follows:

$^1$H NMR (400 MHz, CDCl$_3$) δ 9.02 (d, J=1.6 Hz, 1H), 8.87 (d, J=1.6 Hz, 1H), 8.09 (s, 1H), 7.66-7.56 (m, 2H), 7.55-7.45 (m, 3H). $^{13}$C NMR (101 MHz, CDCl$_3$) δ 151.5, 145.2 (q, J=4.0 Hz), 136.8, 136.3, 131.3 (q, J=3.5 Hz), 129.4, 128.97, 127.30, 126.8 (q, J=32.7 Hz), 123.6 (q, J=272.8 Hz). $^{19}$F NMR (376 MHz, CDCl$_3$) δ −62.40 (s, CF$_3$). HRMS (ESI) calcd. for C$_{12}$H$_9$F$_3$N$^+$ (M+H)$^+$: 224.0682, Found: 224.0679.

Example 10

A method for preparing 2-methyl-3-phenyl-5-trifluoromethylpyridine, comprising the following steps:

S1. in a glove box filled with nitrogen, 8 mg (0.02 mmol, 10.0 mol %) of a catalyst (LA), 1 mL of tetrahydrofuran, 28.2 mg (0.22 mmol, 1.1 equiv) of pinacolborane, and 33.8 mg (0.2 mmol, 1.0 equiv) of 2-methyl-3-phenylpyridine (1g) were added to an 8 mL small reaction flask in this order, and the mixture was stirred and reacted at 40° C. for 4 hours to obtain 2-methyl-3-phenyl-1-(4,4,5,5-tetramethyl-1,3,2-dioxaborolane)-1,4-dihydropyridine, with the reaction formula being as follows:

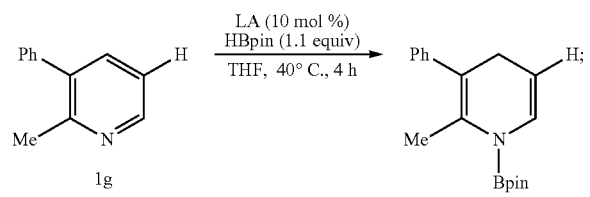

wherein the catalyst LA was the same as in Example 1, i.e., B(2,4,6-F$_3$C$_6$H$_2$)$_3$;

S2. the system was cooled to room temperature, and 69.5 mg (0.22 mmol, 1.1 equiv) of 1-trifluoromethyl-1,2-benziodoxol-3(1H)-one (2c) was added to the above small reaction flask and reacted at room temperature for 1 hours to obtain 2-methyl-3-phenyl-1-(4,4,5,5-tetramethyl-1,3,2-dioxaborolane)-5-trifluoromethyl-1,4-dihydropyridine, with the reaction formula being as follows:

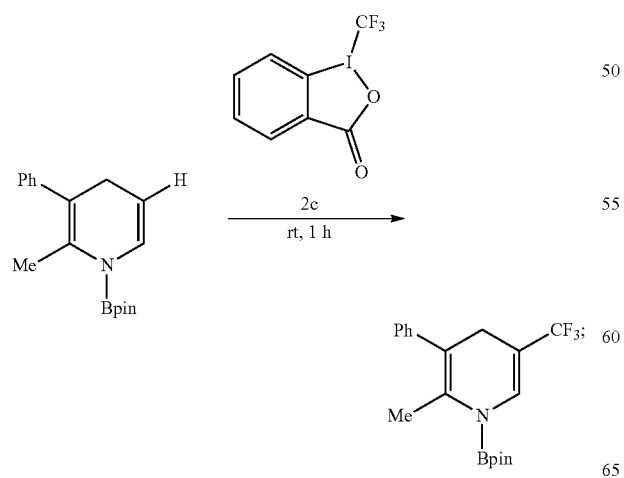

and

S3. the system was cooled to room temperature, the small reaction flask was removed from the glove box, and the system was stirred in the air for 4 hours to produce 2-methyl-3-phenyl-5-(trifluoromethyl)pyridine (3j), with the reaction formula being as follows:

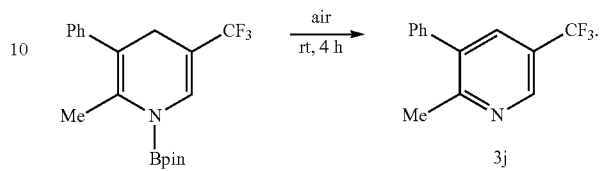

After the reaction was complete, the solvent was removed by rotary evaporation, and the residue was separated and purified by silica gel column chromatography to obtain the product 2-methyl-3-phenyl-5-trifluoromethylpyridine as a colorless oil with a yield of 55%.

The product was characterized as follows:

$^1$H NMR (400 MHz, CDCl$_3$) δ 8.76 (s, 1H), 7.74 (s, 1H), 7.49-7.40 (m, 3H), 7.34-7.29 (m, 2H), 2.57 (s, 3H). $^{13}$C NMR (101 MHz, CDCl$_3$) δ 160.2, 144.6 (q, J=4.1 Hz), 138.4, 137.0, 134.1 (q, J=3.4 Hz), 128.9, 128.7, 128.2, 123.8 (q, J=272.2 Hz), 124.3 (q, J=32.9 Hz), 23.6. $^{19}$F NMR (376 MHz, CDCl$_3$) δ −62.10 (s, CF$_3$). HRMS (ESI) calcd. for C$_{13}$H$_{11}$F$_3$N$^+$ (M+H)$^+$: 238.0838, Found: 238.0839.

What is claimed is:

1. A method for preparing a pyridine compound substituted with trifluoromethylthio, difluoromethylthio, or trifluoromethyl in a meta position, comprising the following steps:

S1. a preparation of 1,4-dihydropyridine or 1,2-dihydropyridine:

in a glove box filled with nitrogen, adding a catalyst, a solvent, pinacolborane, and pyridine to a reaction flask to obtain a first mixture, and stirring the first mixture for a first reaction to obtain dihydropyridine, with a reaction formula being as follows:

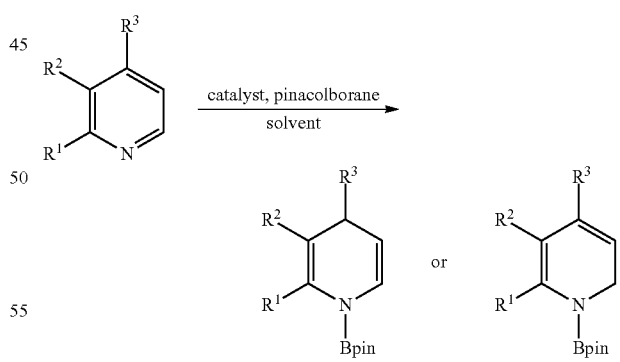

wherein:
the catalyst is triarylboron, a molar ratio of the triarylboron to the pyridine is (5-10): 100, and a structural formula of the triarylboron is B(R$^4$)$_3$ in which R$^4$ is phenyl, pentafluorophenyl, 3,5-bis(trifluoromethyl)-substituted phenyl, or 2,4,6-trifluoro-substituted phenyl;
an equivalent ratio of the pinacolborane to the pyridine is 1.1:1;

the solvent is tetrahydrofuran, dichloromethane, dioxane, 1,2-dichloroethane, or an aromatic solvent; and
a reaction temperature is 40-100° C. and a reaction time is 2-12 hours;

S2. an electrophilic substitution reaction of the dihydropyridine:
adding a trifluoromethylthio reagent, a difluoromethylthio reagent, or a trifluoromethyl reagent to the reaction flask to obtain a second mixture, and stirring the second mixture for a second reaction in a nitrogen atmosphere until the second reaction is complete to obtain dihydropyridine substituted with the trifluoromethylthio, the difluoromethylthio, or the trifluoromethyl in the meta position, with a reaction formula being as follows:

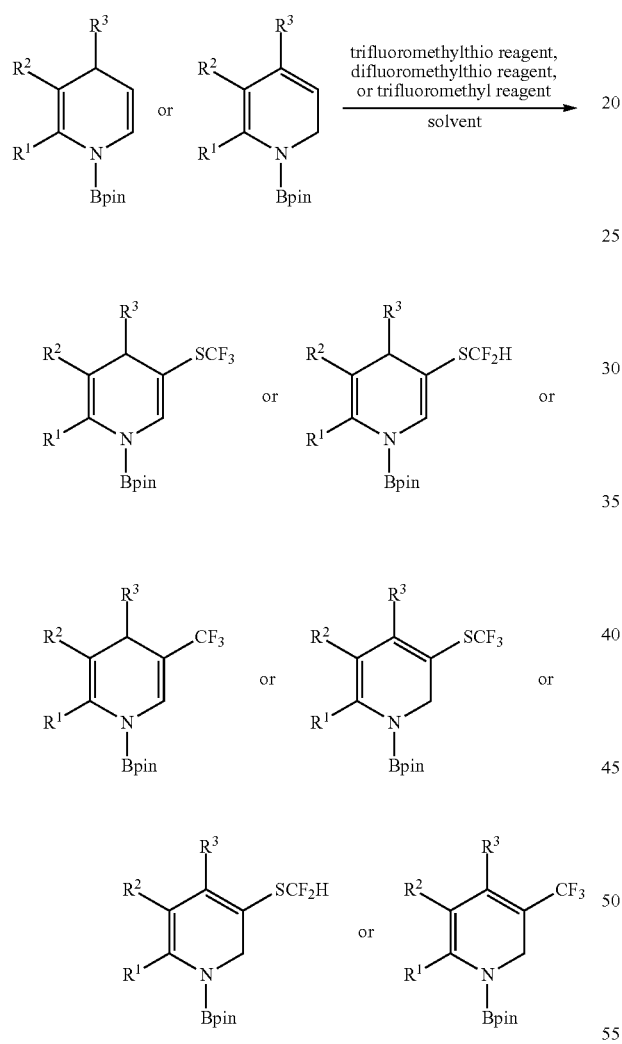

wherein a reaction temperature is room temperature to 80° C., and a reaction time is 2 to 12 hours; and S3. an oxidative aromatization to obtain the pyridine compound substituted with the trifluoromethylthio, the difluoromethylthio, or the trifluoromethyl in the meta position:
placing the reaction flask in an air or adding 2,3-dichloro-5,6-dicyanobenzoquinone to allow a third reaction, stirring until the third reaction is complete, performing a distillation under a reduced pressure to remove the solvent, and then performing a column chromatography separation to obtain the pyridine compound substituted with the trifluoromethylthio, the difluoromethylthio, or the trifluoromethyl in the meta position, with a reaction formula being as follows:

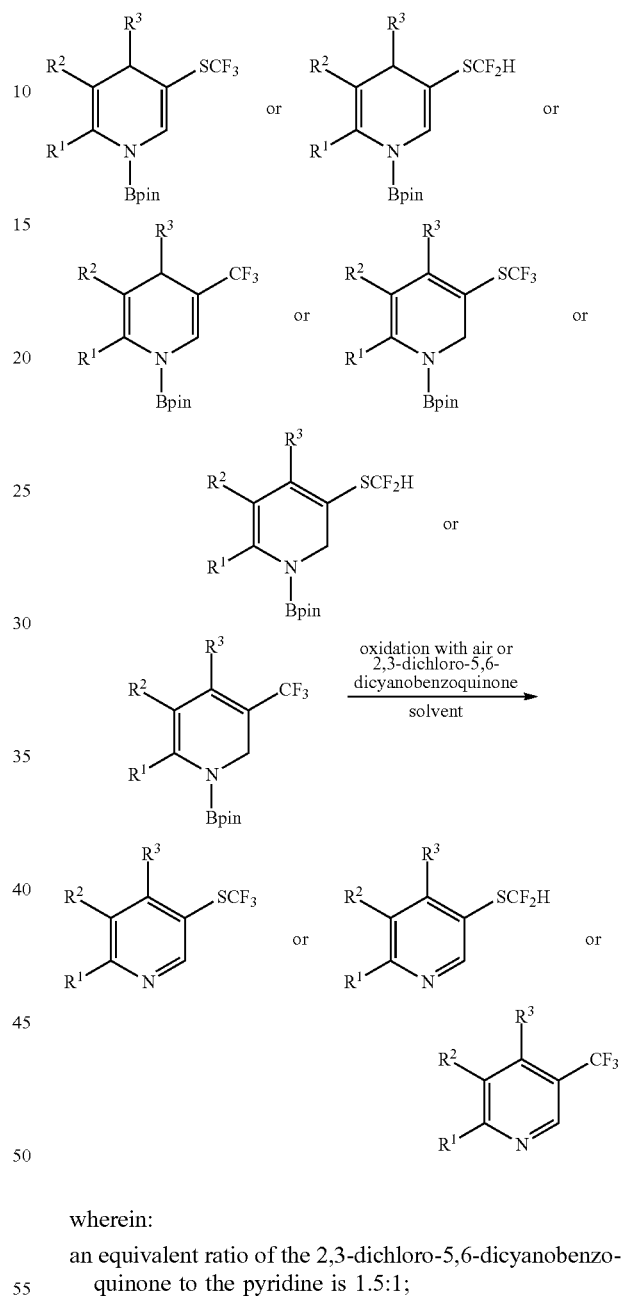

wherein:
an equivalent ratio of the 2,3-dichloro-5,6-dicyanobenzoquinone to the pyridine is 1.5:1;
a reaction temperature is the room temperature, and a reaction time is 4 to 12 hours; and
in the structural formulas of the pyridine, the dihydropyridine, and the pyridine compound substituted with the trifluoromethylthio, the difluoromethylthio, or the trifluoromethyl in the meta position, $R^1$ is hydrogen, alkyl, aryl, substituted aryl, or heteroaryl substituent; $R^2$ is hydrogen, alkyl, halogen, amino, ether group, ester group, aryl, substituted aryl, or heteroaryl substituent; and $R^3$ is hydrogen, alkyl, aryl, substituted aryl, or heteroaryl substituent.

2. The method according to claim 1, wherein in step S2, the trifluoromethylthio reagent is:

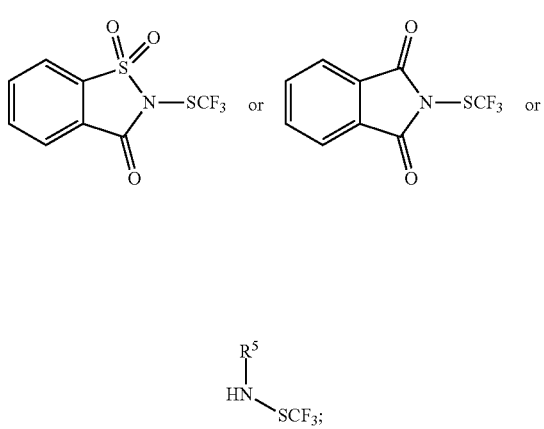

the difluoromethylthio reagent is

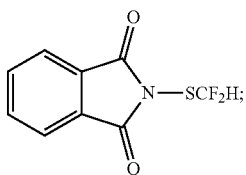

and the trifluoromethyl reagent is

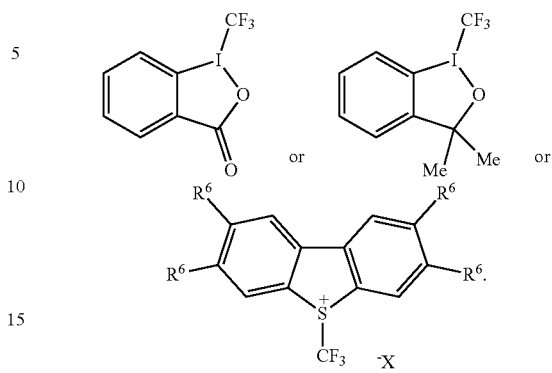

3. The method according to claim 2, wherein the $X^-$ is $BF_4^-$, $TfO^-$, $Cl^-$, $Br^-$, or $I^-$.

4. The method according to claim 2, wherein the $R^5$ is aryl or substituted aryl.

5. The method according to claim 2, wherein the $R^6$ is hydrogen or fluorine.

6. The method according to claim 1, wherein when the $R^1$ is heteroaryl, the heteroaryl is furyl or thienyl.

7. The method according to claim 1, wherein when the $R^2$ is heteroaryl, the heteroaryl is furyl, thienyl, or pyridyl.

8. The method according to claim 1, wherein when the $R^2$ is halogen, the halogen is chlorine, bromine, or iodine.

9. The method according to claim 1, wherein when the $R^3$ is heteroaryl, the heteroaryl is furyl, thienyl, or pyridyl.

* * * * *